United States Patent [19]
Eury

[11] Patent Number: 5,443,458
[45] Date of Patent: Aug. 22, 1995

[54] MULTILAYERED BIODEGRADABLE STENT AND METHOD OF MANUFACTURE

[75] Inventor: Robert P. Eury, Cupertino, Calif.

[73] Assignee: Advanced Cardiovascular Systems, Inc., Santa Clara, Calif.

[21] Appl. No.: 162,670

[22] Filed: Dec. 3, 1993

Related U.S. Application Data

[63] Continuation of Ser. No. 995,529, Dec. 22, 1992, abandoned.

[51] Int. Cl.6 ................................ A61K 9/22
[52] U.S. Cl. .................. 604/891.1; 623/13; 606/198
[58] Field of Search ............... 604/97, 104, 132, 133, 604/285, 288, 891.1, 265; 606/191, 194, 195, 198.7, 8, 151, 153, 155, 108; 623/1, 11, 12, 13

[56] References Cited

U.S. PATENT DOCUMENTS

| | | | |
|---|---|---|---|
| 4,321,711 | 3/1982 | Mano | 3/1.4 |
| 4,743,252 | 5/1988 | Martin, Jr. et al. | 623/1 |
| 4,850,999 | 7/1989 | Planck | 623/1 |
| 4,902,289 | 2/1990 | Yannas | 623/1 |
| 5,028,597 | 7/1991 | Kodama et al. | 514/56 |
| 5,084,065 | 1/1992 | Weldon et al. | 623/1 |
| 5,100,429 | 3/1992 | Sinofsky et al. | 606/195 |
| 5,234,457 | 8/1993 | Andersen | 606/198 |
| 5,282,860 | 2/1994 | Matsuno et al. | 623/12 |
| 5,306,286 | 4/1994 | Stack et al. | 606/198 |
| 5,306,294 | 4/1994 | Winston et al. | 623/1 |
| 5,342,348 | 8/1994 | Kaplan | 604/891.1 |

FOREIGN PATENT DOCUMENTS

| | | |
|---|---|---|
| 0364787A1 | 4/1990 | European Pat. Off. . |
| 0493788A1 | 12/1991 | European Pat. Off. . |
| WO93/06792 | 4/1593 | WIPO . |
| WO89/0323 | 4/1989 | WIPO . |
| WO90/01969 | 3/1990 | WIPO . |
| WO90/04982 | 5/1990 | WIPO . |
| WO90/06094 | 6/1990 | WIPO . |
| WO91/17744 | 11/1991 | WIPO . |
| 9117789 | 11/1991 | WIPO .................. 606/198 |
| WO92/10218 | 6/1992 | WIPO . |

Primary Examiner—C. Fred Rosenbaum
Assistant Examiner—V. Alexander
Attorney, Agent, or Firm—Fulwider Patton Lee & Utecht

[57] ABSTRACT

A stent of multilayered laminated construction wherein one layer addresses the structural requirements of the stent and additional layers release drugs at predictable rates. Both the structural layer as well as the drug releasing layers are eventually completely resorbed by the body.

25 Claims, 1 Drawing Sheet

MULTILAYERED BIODEGRADABLE STENT AND METHOD OF MANUFACTURE

This is a continuation of application Ser. No. 07/995,579, filed Dec. 22, 1992, now abandoned.

BACKGROUND OF THE INVENTION

1. Field of the Invention

The present invention relates to expandable intraluminal vascular grafts, generally referred to as stents. More particularly, the invention pertains to stents that are simultaneously biodegradable and capable of releasing therapeutic drugs.

2. Description of Related Art

Stents are implanted within various lumens vessels of the body in order to maintain the patency of such vessels. A variety of delivery systems have been devised that facilitate the placement and deployment of stents. The stent is initially manipulated while in its contracted state, wherein its reduced diameter more readily allows it to be introduced into the lumen and maneuvered into place. Once in place, it is enlarged to a diameter either greater than or equal to the diameter of the lumen so as to allow the free flow of fluid therethrough.

A system especially adapted for coronary applications employs a stent design that incorporates a combination of interacting elements which serve to automatically lock the stent into its enlarged configuration upon expansion. The stent is moved into position along a previously placed guidewire. Inflation of a balloon about which the stent is held causes the stent to expand and lock. Subsequent deflation of the balloon and withdrawal of the catheter and guide wire leaves the stent in place. Elements extending from the stent's surface engage the vessel walls to positively maintain the stent in position within the lumen.

Stents have heretofore typically been formed of nontoxic, substantially biocompatible metals such as stainless steel, tantalum, or gold. It has however been found that within typically about seven to twenty-one days the endothelial layer of the artery or vessel grows into and throughout the walls of the stent, at which point the stent's utility is substantially diminished and its continued presence may cause any of a variety of problems or complications. It has therefore been proposed to form stents of biodegradable or bioabsorable materials that are completely resorbed by the body within a period of time.

Continued pharmacological treatment of the vessel or condition that made the implantation of the stent necessary is often required or most desirable. Such treatment is typically most effective when administered locally and as a result, it has been suggested to rely on the stent for the delivery of drugs. Materials are known that are capable of absorbing certain drugs and then releasing them at a substantially predictable rate for a predeterminable period of time when subjected to a particular environment. By forming the stent of such drug impregnated material or by otherwise associating such material with the stent, the stent can achieve the dual purpose of maintaining patency while dispensing drugs.

The prior art has been unable to provide a stent that is simultaneously completely resorbable, that possesses the physical properties necessary to facilitate its implantation and to perform its primary function of maintaining the patency of the vessel for a period of time and that gradually releases a drug prior to its resorption. Previous attempts to impart the necessary physical properties to drug-releasing materials or to impart such properties thereto without compromising the drug-releasing properties or the efficacy of the drugs absorbed therein have been unsuccessful.

SUMMARY OF THE INVENTION

The present invention provides a stent that is both completely resorbable within the body as well as capable of delivering certain drugs. Moreover, the stent possesses all the physical properties necessary for it to perform its structural function as well as facilitate its implantation. This is achieved by employing a multi-layered laminated construction. A first resorbable layer is selected for its physical properties. One or more additional resorbable layers are selected for their ability to retain various drugs and then gradually release them upon exposure to the particular environment which they are exposed to upon implantation.

The laminated construction allows a plurality of different drug containing materials to be combined in a single stent. Depending upon the actual configuration of the layers, a simultaneous or sequential release can thereby be achieved. Moreover, different parts of the anatomy can thereby be targeted for treatment by different drugs in that a drug containing layer associated with only the exterior surface of the stent would cause that drug to be released directly into the vessel wall while a drug containing layer associated with only the interior surface of the stent would cause the drug to be released into the lumen.

The stent's laminated construction allows the structural layer to be fabricated prior to lamination. That layer can therefore be subjected to rigorous conditions during its processing and treatment that may be necessary to impart sufficient strength thereto. Such conditions would deteriorate or degrade drugs or drug releasing materials. The present invention provides for the drug impregnated materials to be combined with the structural layer only after the fabrication of the structural layer is complete.

The material selected for the structural layer of the stent of the present invention must be resorbable while providing the necessary physical characteristics. Such requirements can be satisfied by using polymers such as poly-L-lactic acid or polyglycolic acid that have been extruded and oriented to obtain maximum tensile strength and optimal flexural properties.

The drug releasing layers are selected for their ability to retain sufficient quantities of particular drugs, to release those drugs at a constant or at least predictable rate when exposed to the environment encountered upon implantation and to eventually become completely resorbed by the body. Polymers capable of such functions include poly-DL-lactic acid or polycaprolactone. Such polymers are first intermixed with the drug or drugs to be delivered and then are either extruded or solvent cast. The drug containing layer or layers and the structural layer are subsequently laminated to one another using heat or solvents.

The present invention is advantageously applied to stents implantable in a coronary artery after an angioplastic procedure has been performed wherein the exterior surface of the stent releases a drug into the vessel wall which addresses restenosis while an anticoagulant is released into the lumen. Alternatively, a stent according to the present invention may be utilized to treat prostate cancer whereby a chemotherapeutic drug is released directly into the urethra via the stent implanted therein.

These and other features and advantages of the present invention will become apparent from the following detailed description of the preferred embodiments which, taken in conjunction with the accompanying drawings, illustrates by way of example the principles of the invention.

BRIEF DESCRIPTION OF THE DRAWINGS

FIGURE is a perspective view of a stent of the present invention; and

DETAILED DESCRIPTION OF THE PREFERRED EMBODIMENTS

Figure 1:
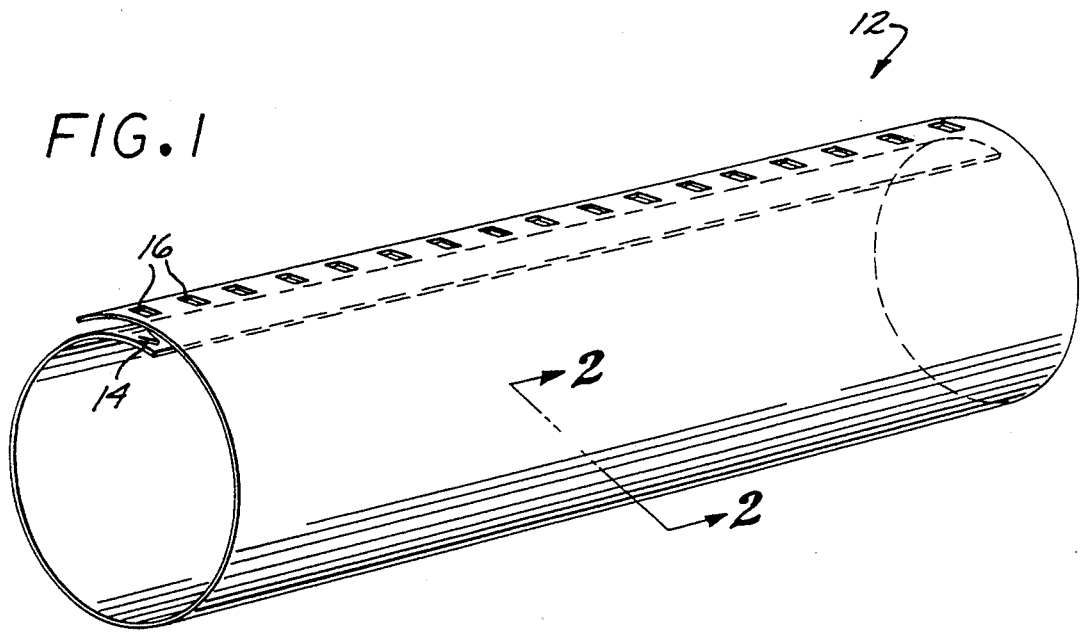

The figures illustrate a preferred embodiment of the present invention. FIG. 1 generally illustrates a stent 12 prior to implantation. The stent is formed as a furled cylinder of sufficiently small outer diameter so as to be transportable through the targeted lumen and of sufficiently large internal diameter to receive a balloon catheter therein. The tabs 14 extending from the catheter's outer surface are sized to engage apertures 16 as the balloon is inflated. Inflation of the balloon causes the cylinder to unfurl and thereby expand. Once elements 14 and 16 have engaged, the stent is effectively locked into its expanded state and cannot recontract.

Figure 2:
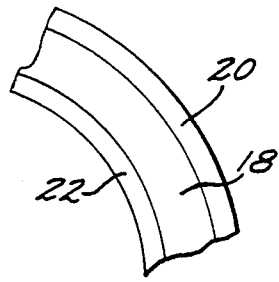
FIG. 2 is an enlarged cross-sectional view showing the laminated construction of the stent of FIG. 1.

FIG. 2 is an enlarged cross-sectional view of the stent 12 according to the present invention. The stent comprises a laminated structure of multiple layers. The particular embodiment illustrated has a total of three layers 18, 20, and 22. The central, relatively thick layer 18 comprises the structural component of the stent which imparts the necessary physical characteristics thereto. This enables the stent to maintain the patency of the vessel into which it is implanted as well as imparts the desired flexural characteristics to the stent to allow it to be moved into position as well as expanded. The thinner layers on either side of the structural layer 18 serve to deliver pharmacological agents. Materials that form these layers are selected for their ability to first absorb drugs and then release them at predictable rates once subjected to the environment encountered upon implantation. In the embodiment illustrated, the layers are disposed such that each is adjacent a surface of the central structural layer 18. These layers may contain the same or different drugs. Alternatively, only one drug releasing layer may be applied to one surface of the stent, or additional drug releasing layers may be built up on top of one another for a sequential release.

The material employed for the structural layer is selected for its ability to impart the necessary physical properties to the stent as well as being completely resorbable by the body. The term resorbable is meant to encompass all those materials that are either biodegradable, bioerodable, or bioabsorbable and includes materials that are broken down and gradually absorbed or eliminated by the body regardless whether such degradation is due mainly to hydrolysis or is mediated by metabolic processes. As previously mentioned—the strength requirements of such material must include the ability for the stent, once in its expanded and locked form, to maintain the patency of the vessel into which it is implanted. Additionally, its physical characteristics must include sufficient flexibility to allow it to be expanded by, for example, the inflation of a balloon contained therein. Furthermore, a degree of longitudinal flexibility is desirable in order to facilitate the stent's transportation via a potentially tortuous path through the lumen to its intended implantation site.

Materials capable of performing both the structural function as well as being resorbable are typically polymeric in nature. Polymers such as poly-L-lactic acid or polyglycolic acid which have been extruded and oriented as per well known methods to obtain maximum tensile strength as well as optimal flexural properties are well-suited for such application. Polyorthoesters as well as polyanhydrides could also be used. The laminated construction of the stent of the present invention allows the structural layer to be processed and treated in an effort to enhance its physical properties without regard to the effect such potentially rigorous conditions would have on drug and drug containing materials.

The materials used for the drug releasing layers 20, 22 are selected for their resorbability as well as for their ability to retain various drugs and subsequently release them at a predictable rate upon being subjected to the environment encountered upon implantation. Materials found to be especially advantageous for such purposes include polymers such as poly-DL-lactic acid and polycaprolactone. Such polymers are intermixed with the drug to be released and subsequently extruded or solvent cast as per well known methods.

After completion of the fabrication of the central structural layer as well as any drug releasing layers, the layers are laminated to one another using heat or solvents. For example, a layer of poly-L-lactic acid and a poly-DL-lactic acid are combinable by subjecting the two layers held in intimate contact with one another to temperatures of about 55° C. The completed laminate is subsequently stamped or laser cut to the appropriate dimensions, while the elements and features necessary to initially maintain the stent in a furled state and subsequently allow it to be locked into its expanded state are formed by similarly well known methods. A final furling or shaping operation renders the stent substantially ready for use.

The dimensions of the stent as well as its ultimate strength and physical characteristics, in addition to the particular drugs and drug delivery rates are of course selected, dependant upon the stent's ultimate purpose. Stents for implantantion in coronary arteries for example would benefit from a stent according to the present invention wherein the inner most layer which is exposed to the lumen releases a drug that addresses thrombosis. An appropriate drug for this purpose includes heparin or prostacyclin. The outer layer 20 in such an application would advantageously release drugs that address restenosis. Drugs that have been found to be effective for this purpose include angiopeptin, methotrexate, as well as heparin.

While a particular form of the invention has been illustrated and described, it will also be apparent to those skilled in the art that various modifications can be made without departing from the spirit and scope of the invention. Any of a variety of stent designs and applications can benefit from the present invention. Accordingly, it is not intended that the invention be limited except by the appended claims.

What is claimed is:

1. A method of fabricating a biodegradable, drug releasing stent for implantation within a lumen, comprising the steps of:

forming a first layer of biodegradable material having physical properties necessary to enable a stent to maintain patency of said lumen;

forming a second layer of biodegradable material which releases a selected drug upon exposure to an environment such as is encountered within said lumen; and superposing said second layer on said first layer to provide a laminated structure that is biodegradable, drug releasing and has the physical properties necessary for said stent to perform its structural function within said lumen.

2. The method of claim 1 further comprising the steps of:

forming a third layer of biodegradable material which releases a selected drug upon exposure to an environment such as is encountered within said lumen; and superposing said third layer to said first layer.

3. The method of claim 2, wherein said second and third layers are joined to said first layer with the application of heat.

4. The method of claim 2 wherein said second and third layers are joined to said first layer with the use of solvents.

5. The method of claim 1, wherein said first layer is formed by extrusion and orientation of a polymeric material.

6. The method of claim 5, wherein said polymeric material comprises poly-L-lactic acid.

7. The method of claim 5 wherein said polymeric material comprises polyglycolic acid.

8. The method of claim 1, wherein said second layer comprises a mixture of said drug and a polymeric material.

9. The method of claim 8 wherein said polymeric material comprises poly-DL-lactic acid.

10. The method of claim 8 wherein a polymeric material comprises a polycaprolactone.

11. The method of claim 1, wherein said second layer is joined to said first layer with the application of heat.

12. The method of claim 1, wherein said second layer is joined to said first layer with the use of solvents.

13. An expandable stent for implantation in a vessel, comprising:

a first layer formed of a first resorbable material selected to impart structural rigidity to said stent for maintaining patency of the vessel; and second layer formed of a second resorbable material, superposed on and laminated to said first layer and selected to release a therapeutic drug at a predictable rate upon implantation; said first layer and said second layer rolled up to form a cylinder for delivery to the site at which the stent is to be implanted; and said stent providing a desired degree of structural support to said vessel, and releasing said drug at said predictable rate.

14. The stent of claim 13, wherein said material of said first layer further is selected to impart high tensile strength to said stent.

15. The stent of claim 13, wherein said first layer comprises poly-L-lactic acid.

16. The stent of claim 13, wherein said first layer comprises polyglycolic acid.

17. The stent of claim 13, wherein said second layer comprises poly-DL-lactic acid.

18. The stent of claim 13, wherein said second layer comprises polycaprolactone.

19. The stent of claim 13, wherein said stent is implantable in a lumen upstream from a cancerous growth and said second layer is selected to release a chemotherapeutic drug.

20. The stent of claim 13, wherein said second layer is selected to release heparin.

21. The stent of claim 20, wherein said second layer is selected to release angiopeptin, and said third layer is selected to release heparin.

22. The stent of claim 13, wherein a third layer of resorbable material is superposed on and laminated to said first layer and selected to release a therapeutic drug at a predictable rate therefrom, whereby upon implantation, said stent initially provides a desired degree of structural support to said vessel, releases said drugs at the predictable rates, and eventually is completely resorbed.

23. The stent of claim 22, wherein the drugs released by said second and said third layer are identical.

24. The stent of claim 22, wherein the drugs released by said second and said third layer are different.

25. The stent of claim 24, wherein said stent is implantable within a coronary artery, said second layer is superposed on and laminated to the outer side of said stent's first layer and releases a drug that addresses restenosis, and said third layer is superposed on and laminated to the inner side of said stent's first layer and releases a drug that addresses thrombosis.

* * * * *

UNITED STATES PATENT AND TRADEMARK OFFICE
CERTIFICATE OF CORRECTION

PATENT NO. : 5,443,458
DATED      : August 22, 1995
INVENTOR(S) : Robert P. Eury It is certified that error appears in the above-indentified patent and that said Letters Patent is hereby corrected as shown below:

Column 3, line 12, change "FIGURE" to read -- FIG. 1 --.

Signed and Sealed this

Twentieth Day of May, 1997

Attest:

BRUCE LEHMAN

*Attesting Officer*  *Commissioner of Patents and Trademarks*